United States Patent [19]

Tenygl

[11] Patent Number: 4,601,792
[45] Date of Patent: Jul. 22, 1986

[54] METHOD FOR ELECTROANALYTICAL DETERMINATION OF ELECTROCHEMICALLY ACTIVE COMPOUNDS IN SOLUTION

[75] Inventor: Jiří Tenygl, Prague, Czechoslovakia

[73] Assignee: Ceskoslovanka Akademie Ved, Praha, Czechoslovakia

[21] Appl. No.: 774,247

[22] Filed: Sep. 9, 1985

[30] Foreign Application Priority Data

Sep. 10, 1984 [CS] Czechoslovakia ............ 6781-84

[51] Int. Cl.$^4$ ............................................. G01N 27/48
[52] U.S. Cl. ........................................ 204/1 T; 204/413
[58] Field of Search ............................. 204/413, 1 T

[56] References Cited

U.S. PATENT DOCUMENTS 4,260,467  4/1981  Smith et al. .................... 204/413

OTHER PUBLICATIONS

R. Dias et al., J. Electroanal. Chem., 130, pp. 345–349, (1981).

Primary Examiner—G. L. Kaplan

[57] ABSTRACT

The invention relates to an improved and highly sensitive method of electroanalytical determination of electrochemically active compounds in solution. The invention comprises a pulsating mercury drop to obtain polarographic, voltametric (coulometric), potentiometric, and anodic stripping measurements, and other measurements derived therefrom. According to the invention, a pulsating mercury drop is extruded from a capillary tube into an electrochemical solution to be evaluated, and its electrolytic current or potential is measured against a reference electrode. The method provides that mercury is extruded from the capillary (and the size of the drop is increased) and then it is withdrawn back into the capillary (and the drop is decreased to its original size), so that the drop pulsates at a frequency of 0.1 to 100 cycles/second. In addition, the potential of the drop is varied continuously, or is changed by a jump from a value where oxidation or reduction of the measured electrochemical compound occurs, to a value where anodic dissolution results in deposition of the measured compound.

9 Claims, No Drawings

METHOD FOR ELECTROANALYTICAL DETERMINATION OF ELECTROCHEMICALLY ACTIVE COMPOUNDS IN SOLUTION

The invention relates to an improved and highly sensitive method of electroanalytical determination of electrochemically active compounds in solution.

BACKGROUND OF THE INVENTION

The invention comprises a pulsating mercury drop to obtain polarographic, voltametric (coulometric), potentiometric, and anodic stripping measurements, and other measurements derived therefrom. A pulsating mercury drop is extruded from a capillary tube into an electrochemical solution to be evaluated, and its electrolytic current or potential is measured against a reference electrode. The method provides that mercury is extruded from the capillary (and the size of the drop is increased) and then it is withdrawn back into the capillary (and the drop is decreased to its original size), so that the drop pulsates at a frequency of 0.1 to 100 cycles/second. In addition, the potential of the drop is varied continuously, or is changed by a jump from a value where oxidation or reduction of the measured electrochemical compound occurs, to a value where anodic dissolution results in deposition of the measured compound.

A known device is described in Dias et al, *Pulsed Flow mercury Electrode*, J. Electroanal. Chem. No. 130, pp 345–9 (1981).

Polarographic measuring devices are known, and are based on principals first developed by the Czechoslovak chemist Jaroslav Heyrovsky. In its simplest form, a polarograph is an instrument that photographically records minute changes in the intensity of a current resulting from a gradually increasing applied voltage, in electrolysis with a dropping mercury cathode. The polarograph is typically used to measure the deposition or reduction of cations and anions, voltage gradients, solubility, ionic complexity; and is useful for qualitative and quantitative microanalysis.

Voltametric, or coulombic analysis is also known as a method of measuring current intensity by electrolysis. Potentiometric analysis relates to the continuous measurement of the potential of an electrode immersed in a solution to be evaluated. A rapid change in potential typically indicates the end of the electrochemical reaction.

A polarographic measurement of a dropping mercury electrode may be obtained by known methods, whereby the regeneration of surface compounds and the removal of deposited compounds is evaluated by reference to the dripping mercury; with the measurements carried out on a fresh mercury surface. Suitably reproducible results can be obtained with this method, but the relatively rapid consumption of mercury, which must be purified prior to each use, is a distinct disadvantage. From the electrochemical point of view, another disadvantage is that the newly created drop must be electrically charged to a measurement potential. This charge becomes manifest as a capacity current that is summed with the faradic current corresponding to the electrochemical oxidation/reduction potential of the measured compound. The added charge reduces the sensitivity of the method and device.

Numerous methods of avoiding the charging current have been suggested. For example, one method would be to measure against a small changing surface of mercury, or against a stationary mercury drop.

SUMMARY OF THE INVENTION

The present novel method comprises the measurement of the current potential of a pulsating mercury drop. The size of the drop varies during the measurement such that the drop expands as mercury is extruded from a capillary tube and then contracts to its original size as mercury is retracted into the tube, with a frequency of 0.1 to 100 cycles/second.

Another advantageous feature of the method is that the surface of the mercury drop can be regenerated during measurement by changing the potential gradient, either continuously or by an integral jump from the point where oxidation or reduction begins to the point where anodic dissolution occurs, this being the point where compounds which are separated from the measured solution and deposited on the surface of the mercury drop, or which are dissolved within its mass in the form of an amalgam, are again released to the solution.

The method, according to the invention, is advantageous for a number of reasons. First, the effect of any capacity current on the faradic current (the measuring current) is substantially suppressed. During the successive expansion and contraction of the mercury drop, the capacity current passing in the positive direction is equal to the capacity current passing in the negative direction, and the two currents cancel each other out. There is no net capacity current flowing in the external circuit during pulsation of the drop. A rapidly responding oscillating recorder, which might record the passage of the capacity current in both directions, can be made to suppress the capacity current by means of a capacitor connected in parallel, through which the excess current potential is cancelled.

A second advantage follows from elimination of the capacity current by means of a pulsating drop. The method of the invention is more sensitive than classical polarography by about two orders of magnitude. Moreover, the cancellation of the detrimental capacity current and the improvement in sensitivity are achieved in a simple and economical way.

Another advantage of the invention resides in the fact that the measurement is carried out on the moving mercury surface. The drop pulsation cancels the concentration polarization and increases the convection transport of a depolarizer to the mercury surface, further assisting in the increased sensitivity of the method. At the same time, dependence of the measurement current on a translation rate of sample flow along the pulsating drop is advantageously reduced.

Yet another advantage of the present method is the continuous regeneration of the drop surface resulting from its pulsation. This is achieved by a combination of factors, mainly by desorption and agitation of the mercury such that the continuous formation of a passive film is prevented. If heavy contamination of the mercury surface should occur, the foul drop can be readily removed by allowing it to drip from the capillary tube, to be replaced by a new drop which is extruded from the tube.

The surface of the mercury drop can be regenerated electrochemically, and during measurement, by changing the potential of the drop. This is achieved by maintaining a continuous variation in measurement potential, or by causing the potential to jump from a redox value to a potential that results in anodic dissolution of compounds deposited on the surface of the mercury or dissolved in its mass as an amalgam. Both potentials depend on the electrochemical potential of the deposited compounds and on the composition of the specific solution being evaluated.

Simple electrochemical regeneration during measurement may be induced in a common polarograph. However, the present invention combines the pulsating mercury drop with a mercury dropping electrode to achieve rapid, continuous, and automatic regeneration in a manner heretofore unknown. The pulsating drop is polarized from a potential of $-0.1$ V against a saturated calomel electrode (SCE) towards negative potentials of about $-1.5$ V (SCE) at a rate of 400 mV/min. A curve representing the dependence of current on potential is recorded; and this curve is seen to be the same as in classical polarography.

For example, in the presence of cadmium (II) ions, the curve exhibits a wave of polarographic reduction of $Cd^{2+}$ to Cd. At a potential of $-1.5$ V (SCE) the directions of the polarization is reversed, and the pulsating drop electrode is polarized at the same rate back towards a potential of $-0.1$ V (SCE). When the electrochemical potential of cadmium amalgam is reached, dissolution occurs and is manifested as a characteristic anodic current peak. At the same time, dissolution of cadmium occurs and the surface of the pulsating drop is regenerated. The same regeneration occurs even when the potential of the pulsating drop is changed by a jump in value from $-1.3$ V (SCE) to $-0.1$ V (SCE).

This combined effect permits continuous measurement with the pulsating drop for several hours, and sometimes even for days, without the formation of a passive surface. When a simple mercury dropping electrode is used, the anodic dissolution peak is not formed. Therefore, the pulsating mercury drop extends the possible analytical utilization of electrochemical methods. In addition, it is advantageous that, according to the invention, the heights of the cathodic wave and the anodic dissolution peak are directly proportional to the concentration of depolarizer in a sample.

The frequency of pulsation depends on the application. A rapid pulsation, such as from 5 to 100 cycles/second, increases the sensitivity of the measurement, suppresses oscillations generated by the measuring device, and is preferred for electroanalysis. Slower pulsations, such as from 0.1 to 1 cycle/second are preferable for the investigation of electrochemical processes.

The desired pulsation is maintained by extrusion and retraction of the mercury drop with respect to a capillary tube, and this in turn is achieved by connecting the capillary tube to a source of mechanical oscillations, such as a piston, a diaphragm, a peristaltic device, etc. The size of the drop is determined by the diameter of the capillary tube, and may reach a maximum size of five times the tube diameter.

The amount of extruded and retracted mercury depends on the diameter of the capillary, and the volume of the drop typically ranges from 0.01 to 100 microliters. Small amounts, such as 0.01 to 10 microliters are useful for laboratory measurements. Larger amounts, such as 1000 microliters and more, are useful for industrial applications. With larger amounts, the drop does not retain a spherical shape, and does not hang in the test solution in the form of a drop. Instead, it is extruded into a capillary tube with a conical outlet having a diameter of several millimeters.

The method of the invention is illustrated by the following examples. It will be evident to practitioners in the art that these examples do not serve to limit the scope of the invention or the appended claims.

EXAMPLE 1

Polarographic determination of low (ppm) concentrations of zinc and nickel.

A 0.1 M KCl solution contains 1 ppm $Ni^{2+}$ and 2 ppm $Zn^{2+}$. The determination is carried out by polarography, using a pulsating drop according to the invention. The drop is pulsating at a frequency of 3 cycles/second, the diameter of the capillary is 0.5 mm, and the volume of the extruded mercury is 5 microliters. After removal of oxygen, a first polarographic curve is recorded with the potential of the pulsating drop being varied from $-0.2$ V (SCE) to $-1.5$ (SCE) at a rate of 200 mV/min. The sense of polarization changes at $-1.5$ V (SCE), and a second polarographic curve was obtained from $-1.5$ V (SCE) back to $-0.2$ V (SCE). The recording of both curves is repeated with standard solutions of $Zn^{2+}$ and $Ni^{2+}$ added. Both metals are reduced in a single wave with respect to a small difference in their half-wave potentials. The first curve corresponds to the reduction of nickel and zinc. The second curve records the oxidation peak of zinc amalgam without the interference of nickel, which is dissolved first at a much more positive potential with respect to the irreversibility of the anodic reaction. The concentration of nickel is obtained from the first curve after subtraction of the concentration of zinc determined from the second curve.

The determination according to this example is about 80 time more sensitive than a determination made by classical polarography. Moreover, the pulsating mercury drop permits the simultaneous evaluation of two metal ions in solution from a single composite curve consisting of two parts. This result is impossible with a mercury dropping electrode, because the known technology requires the prior separation of both metals.

EXAMPLE 2

Continuous determination of reducible compounds in high-performance liquid chromatography (HPLC).

In this embodiment, the pulsating mercury drop is connected to a polarograph terminal instead of to a dropping mercury electrode. The reference electrode is a silver wire coated with a layer of silver chloride (AgCl) which is wound around a glass capillary tube. The pulsating drop electrode is charged to a potential of $-1.7$ V with respect to the reference electrode. Effluent from a chromatographic column flows along the pulsating drop electrode at a rate of 1 ml/min.

The shape of the vessel and the arrangement of the electrodes may be varied according to the specific application, and are not essential to the method of the invention as described and claimed herein. Changes in shape and geometry may affect the response time of the electrode with respect to changes in the concentration the components being evaluated, but will not affect the value of the passing current or its time stability.

Reduction of compounds separated in the chromatographic column occurs while the effluent passes along the pulsating drop electrode. The reduction current is recorded by a polarograph recorder, and characteristic peaks appear in the record of current against time, which in turn correspond to the increase and subsequent decrease in the concentration of electrochemically active compounds in the effluent in the sequence of their prior HPLC separation.

Upon completion of the recording, and after the effluent has passed, compounds deposited on or dissolved in the pulsating mercury drop can be determined by means of the pulsating drop electrode. The pulsating mercury drop is polarized at the rate of 100 to 1000 mV/min. up to the potential $-0.05$ V. During polarization towards a positive potential, anodic dissolution of metals occurs. These metals, such as $Zn^{2+}$, $Cd^{2+}$, $Tl^{2+}$, $Pb^{2+}$, $Cu^{2+}$, were deposited from the effluent and formed amalgams. The metals are dissolved in sequence depending on their electrochemical potentials. The height of the amalgam anodic dissolution peaks is proportional to the amount of ions of the corresponding metals in the effluent. Further resolution of the deposited metals can be obtained in this way by comparison to the mercury dropping electrode.

These examples do not exhaust the possible applications of the invention. For example, the present method is also useful for the continuous determination of the concentration of pollutants in air and water, for the monitoring and control of industrial substances, and for a number of other applications.

We claim:

1. A polarographic, voltametric, potentiometric and anodic method for electroanalytical determination of electrochemically active compounds in solution comprising the steps of:
   extruding a mercury drop from a capillary tube and retracting the drop back toward the tube to generate a pulsating mercury drop which expands and contracts at a frequency of 0.1 to 100 cycles per second;
   placing the pulsating mercury drop into a solution to be measured; and
   measuring the current potential of the pulsating drop against a reference electrode to determine the electrochemical activity of one or more components in solution.

2. A method as in claim 1 comprising the additional step of regenerating the pulsating drop by continuously changing its potential from a value at which oxidation or reduction of a component in solution occurs to a value at which anodic dissolution occurs.

3. A method as in claim 1 comprising the additional step of regenerating the pulsating mercury drop by changing its potential in a jump from a value at which oxidation or reduction of a component in solution occurs to a value at which anodic dissolution occurs.

4. A method as in claim 1 wherein the reference electrode is a saturated calomel electrode.

5. A method as in claim 1 wherein the reference electrode is a silver wire coated with a layer of silver chloride (AgCl) which is wound around the capillary tube.

6. A method as in claim 1 wherein the pulsations of the mercury drop are mechanically generated.

7. A method as in claim 1 wherein the volume of the mercury drop may range from 0.01 to 100 microliters.

8. A polarographic, voltametric, potentiometric and anodic method for electroanalytical determination of electrochemically active compounds in solution comprising the steps of:
   extruding a mercury drop from a capillary tube and retracting the drop back toward the tube to mechanically generate a pulsating mercury drop which expands and contracts at a frequency of 0.1 to 100 cycles per second;
   placing the pulsating mercury drop into a solution to measured;
   measuring the current potential of the pulsating drop against a reference electrode to determine the electrochemical activity of one or more components in solution; and
   changing the potential of the pulsating mercury drop from a value at which oxidation or reduction of a component in solution occurs to a value at which anodic dissolution occurs.

9. A polarographic, voltametric, potentiometric and anodic method for electroanalytical determination of electrochemically active compounds in solution comprising the steps of:
   extruding a mercury drop from a capillary tube and retracting the drop back toward the tube to mechanically generate a pulsating mercury drop which is from 0.01 to 100 microliters in volume and which expands and contracts at a frequency of 0.1 to 100 cycles per second;
   placing the pulsating mercury drop into a solution to measured;
   measuring the current potential of the pulsating drop against a reference electrode selected from the group consisting of a saturated calomel electrode and a silver wire coated with a layer of silver chloride (AgCl) wound around the capillary tube, to determine the electrochemical activity of one or more components in solution; and
   changing the potential of the pulsating mercury drop from a value at which oxidation or reduction of a component in solution occurs to a value at which anodic dissolution occurs.

* * * * *